(12) United States Patent
Karpov et al.

(10) Patent No.: US 11,400,437 B2
(45) Date of Patent: Aug. 2, 2022

(54) CATALYST FOR THE OXIDATION OF ETHYLENE TO ETHYLENE OXIDE

(71) Applicant: BASF SE, Ludwigshafen am Rhein (DE)

(72) Inventors: Andrey Karpov, Ludwigshafen am Rhein (DE); Michael Kraemer, Ludwigshafen am Rhein (DE); Marco Bosch, Ludwigshafen am Rhein (DE); Christian Bartosch, Ludwigshafen am Rhein (DE); Juergen Zuehlke, Ludwigshafen am Rhein (DE); Carlos Lizandara Pueyo, Ludwigshafen am Rhein (DE); Guido Wasserschaff, Neckargemünd (DE)

(73) Assignee: BASF SE, Ludwigshafen am Rhein (DE)

( * ) Notice: Subject to any disclaimer, the term of this patent is extended or adjusted under 35 U.S.C. 154(b) by 607 days.

(21) Appl. No.: 16/323,828

(22) PCT Filed: Aug. 8, 2017

(86) PCT No.: PCT/EP2017/070054
§ 371 (c)(1),
(2) Date: Feb. 7, 2019

(87) PCT Pub. No.: WO2018/029189
PCT Pub. Date: Feb. 15, 2018

(65) Prior Publication Data
US 2021/0283583 A1 Sep. 16, 2021

(30) Foreign Application Priority Data

Aug. 8, 2016 (EP) ..................... 16183180

(51) Int. Cl.
*B01J 23/68* (2006.01)
*B01J 6/00* (2006.01)
(Continued)

(52) U.S. Cl.
CPC ............. *B01J 23/688* (2013.01); *B01J 6/001* (2013.01); *B01J 23/04* (2013.01); *B01J 35/1009* (2013.01);
(Continued)

(58) Field of Classification Search
None
See application file for complete search history.

(56) References Cited

U.S. PATENT DOCUMENTS

| 3,962,136 A | 6/1976 | Nielsen et al. |
| 4,007,135 A | 2/1977 | Hayden et al. |

(Continued)

FOREIGN PATENT DOCUMENTS

| CA | 1026763 A | 2/1978 |
| CN | 102029154 A | 4/2011 |

(Continued)

OTHER PUBLICATIONS

U.S. Appl. No. 16/311,015, Bohres et al.
(Continued)

*Primary Examiner* — Colin W. Slifka
(74) *Attorney, Agent, or Firm* — Faegre Drinker Biddle & Reath LLP

(57) ABSTRACT

The present invention is directed to a shaped catalyst body for preparing ethylene oxide, which comprises at least silver, cesium and rhenium applied to an alumina support, wherein the alumina support comprises Si, Ca, and Mg in a defined amount. Furthermore, the present invention is directed to a process for preparing the catalyst according to the present invention and process for preparing ethylene oxide by
(Continued)

gas-phase oxidation of ethylene by means of oxygen in the presence of a shaped catalyst body according to the present invention.

19 Claims, 1 Drawing Sheet

(51) Int. Cl.
*B01J 23/04* (2006.01)
*B01J 35/10* (2006.01)
*B01J 37/02* (2006.01)
*C07D 301/10* (2006.01)
*B01J 21/10* (2006.01)
*B01J 21/12* (2006.01)

(52) U.S. Cl.
CPC ......... *B01J 35/109* (2013.01); *B01J 35/1066* (2013.01); *B01J 35/1071* (2013.01); *B01J 35/1076* (2013.01); *B01J 37/0205* (2013.01); *B01J 37/0207* (2013.01); *C07D 301/10* (2013.01); *B01J 21/10* (2013.01); *B01J 21/12* (2013.01)

(56) References Cited

U.S. PATENT DOCUMENTS

| | | |
|---|---|---|
| 4,324,699 A | 4/1982 | Mross et al. |
| 4,389,338 A | 6/1983 | Mitsuhata et al. |
| 4,732,918 A | 3/1988 | Lohmueller et al. |
| 4,766,105 A | 8/1988 | Lauritzen |
| 4,774,222 A | 9/1988 | Rashkin |
| 5,011,809 A | 4/1991 | Herzog et al. |
| 7,560,577 B2 | 7/2009 | Hirota et al. |
| 7,977,274 B2 | 7/2011 | Gueckel |
| 2009/0177016 A1 | 7/2009 | Lockemeyer et al. |
| 2009/0198076 A1 | 8/2009 | Guckel |
| 2009/0270640 A1 | 10/2009 | Maurer et al. |
| 2010/0191006 A1 | 7/2010 | Guckel |
| 2012/0264954 A1 | 10/2012 | Rosendahl et al. |
| 2013/0296587 A1 | 11/2013 | Rosendahl et al. |
| 2014/0100379 A1 | 4/2014 | Richard et al. |
| 2017/0008867 A1 | 1/2017 | Galeano Nunez et al. |
| 2017/0333877 A1 | 11/2017 | Titlbach et al. |
| 2018/0008962 A1 | 1/2018 | Galeano Nunez et al. |
| 2018/0021756 A1 | 1/2018 | Karpov et al. |
| 2018/0021757 A1 | 1/2018 | Karpov et al. |
| 2018/0071679 A1 | 3/2018 | Karpov et al. |
| 2018/0104674 A1 | 4/2018 | Grüne et al. |

FOREIGN PATENT DOCUMENTS

| | | |
|---|---|---|
| CN | 103596677 A | 2/2014 |
| DE | 2300512 A1 | 7/1973 |
| DE | 2454972 A1 | 6/1975 |
| DE | 2521906 A1 | 12/1975 |
| DE | 2753359 A1 | 6/1979 |
| DE | 3150205 A1 | 8/1982 |
| DE | 3321895 A1 | 12/1983 |
| DE | 3414717 A1 | 10/1985 |
| DE | 2560684 C2 | 10/1989 |
| EP | 0011356 A1 | 5/1980 |
| EP | 0014457 A2 | 8/1980 |
| EP | 0082609 A1 | 6/1983 |
| EP | 0085237 A1 | 8/1983 |
| EP | 0172565 A2 | 2/1986 |
| EP | 229465 A1 | 7/1987 |
| EP | 0339748 A2 | 11/1989 |
| EP | 0357293 A1 | 3/1990 |
| EP | 384312 A1 | 8/1990 |
| EP | 0266015 B1 | 12/1991 |
| EP | 0480538 A1 | 4/1992 |
| EP | 0496470 A1 | 7/1992 |
| EP | 1308442 B1 | 2/2008 |
| EP | 1955766 A1 | 8/2008 |
| JP | 2009-525871 A | 7/2009 |
| JP | 2009-525938 A | 7/2009 |
| JP | 2014-512949 A | 5/2014 |
| WO | WO-2007122090 A2 | 11/2007 |
| WO | WO-2010123856 A | 10/2010 |
| WO | 2012/140613 A1 | 10/2012 |
| WO | WO-2013061294 A1 | 5/2013 |
| WO | WO-2016096990 A1 | 6/2016 |

OTHER PUBLICATIONS

U.S. Appl. No. 16/320,572.
U.S. Appl. No. 16/323,828, Karpov et al.
Park, C.W., et al., "Effects of $SiO_2$, $CaO_2$, and MgO Additions on the Grain Growth of Alumina", Journal of the American Ceramic Society, vol. 83, No. 10, (2000), pp. 2605-2609.
International Preliminary Examination Report for PCT/EP2017/070054 dated Nov. 2, 2018.
International Preliminary Report on Patentability for PCT/EP2017/070054 dated Nov. 23, 2017.
Rebsdat, S., et al., "Ethylene Oxide" in Ullmann's Encyclopedia of Industrial Chemistry, 5th edition, eds. Gerhartz, et al., VCH-Verlagsgesellschaft: Weinheim, 1987, vol. A-10, pp. 117-135.
Park, C. W., et al., "Effects of $SiO_2$, $CaO_2$, and MgO Additions on the Grain Growth of Alumina", Journal of the American Ceramic Society, 2000, vol. 83, No. 10, pp. 2605-2609.

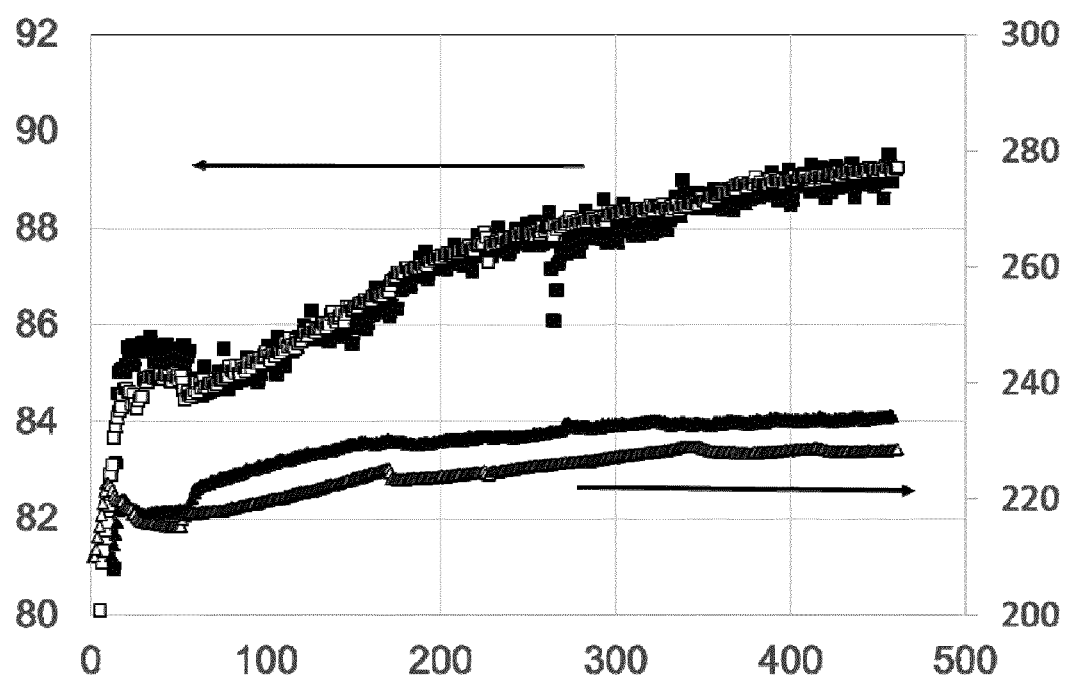

CATALYST FOR THE OXIDATION OF ETHYLENE TO ETHYLENE OXIDE

CROSS-REFERENCE TO RELATED APPLICATIONS

This application is a national stage application (under 35 U.S.C. § 371) of PCT/EP2017/070054, filed Aug. 8, 2017, which claims benefit of European Application No. 16183180.5, filed Aug. 8, 2016, both of which are incorporated herein by reference in their entirety.

The present invention is directed to a shaped catalyst body for preparing ethylene oxide, which comprises at least silver, cesium and rhenium applied to an alumina support, wherein the alumina support comprises Si, Ca, and Mg in a defined amount. Furthermore, the present invention is directed to a process for preparing the catalyst according to the present invention and process for preparing ethylene oxide by gas-phase oxidation of ethylene by means of oxygen in the presence of a shaped catalyst body according to the present invention.

Ethylene oxide is an important basic chemical and frequently prepared on an industrial scale by direct oxidation of ethylene with oxygen in the presence of silver-containing catalysts. These catalysts usually comprise metallic silver and further elements, which have been deposited on a support material by means of a suitable process.

Apart from silver as active component, these catalysts often comprise promoters for improving the catalytic properties (WO 2007/122090, WO 2010/123856). Examples of promoters are alkali metal compounds and/or alkaline earth metal compounds. Some documents teach the use of transition metals such as cobalt (EP 0 480 538), tungsten or molybdenum. A particularly preferred promoter for influencing the activity and selectivity of catalysts is rhenium. In industry, preference is given to using catalysts comprising rhenium and/or other transition metal promoters in combination with alkali metal compounds and/or alkaline earth metal compounds because of their high selectivity. Selectivity is, for example in the case of the oxidation of ethylene, the molar percentage of ethylene which reacts to form ethylene oxide. The activity of the catalyst is usually characterized by the ethylene oxide concentration at the reactor outlet under otherwise constant conditions, for example temperature, pressure, gas throughput, amount of catalyst, etc. The higher the ethylene oxide concentration in the reactor output stream, the higher the activity of the catalyst. The lower the temperature required for achieving a predetermined ethylene oxide concentration, the higher the activity.

The direct oxidation of ethylene to ethylene oxide using supported silver catalysts is described, for example, in DE-A-2300512, DE-A 2521906, EP-A-0014457, DE-A-2454972, EP-A-0172565, EP-A-0357293, EP-A-0266015, EP-A-0011356, EP-A-0085237, DE-A-2560684 and DE-A -2753359.

As supports, it is in principle possible to use various porous materials such as activated carbon, titanium dioxide, zirconium dioxide or silicon dioxide or ceramic compositions or mixtures of these materials. In general, alpha-aluminum oxide is used as support.

EP 0 266 015 B1 discloses a catalyst composition, suitable for the catalytic manufacture of ethylene oxide from ethylene and oxygen, containing silver and a support, characterized in that the catalyst composition comprises a promoting amount of rhenium or compound thereof, a promoting amount of at least one further metal or compound thereof and that the support has a surface area of less than 20 m$^2$/g. Table 5 of EP 0 266 015 B1 discloses a series of catalysts with Re-concentration in the range of 0 to 744 ppmw, Cs-concentration in the range of 236 to 634 ppmw prepared using a carrier with surface area of 0.42 m$^2$/g.

It is in principle possible to use alpha-aluminum with a wide-range of physical properties as support material. Typically, supports with relatively low surface area (<10 m$^2$/g) and either a mono-modal or bi-modal pore distribution are preferred. For example, U.S. Pat. No. 7,560,577 B2 and U.S. Pat. No. 7,977,274 B2 disclose the use of a support with a two log differential pore volume distribution peaks in a pore diameter range of 0.01-100 µm and 1-20 µm, respectively, and at least one peak in a pore diameter range of 0.01-1.0 µm and 0.1-5 µm, respectively, measured by mercury porosimetry.

EP 0 496 470 A1 discloses an ethylene oxide catalyst for the vapor phase production of ethylene oxide from ethylene and oxygen comprising a catalytically effective amount of silver, a promoting amount of alkali metal and a promoting amount of rhenium supported on a carrier comprising at least 85 percent by weight of alpha alumina, from 0.05 to 6 percent by weight (measured as the oxide, MO) of an alkaline earth metal in the form of an oxide, from 0.01 to 5 percent by weight (measured as the dioxide) of silicon in the form of an oxide and from zero to 10 percent by weight (measured as the dioxide) of zirconium in the form of an oxide. Furthermore, EP 0 496 470 A1 discloses the carrier water pore volume between 0.2 and 0.6 cc/g and a surface area between 0.15 and 3 m$^2$/g.

EP 1 308 442 B1 discloses a catalyst for the production of ethylene oxide, having a silver deposited on a carrier containing at least 90.0 mass % of α-alumina, 0.03%-0.8 mass % of potassium and iron (calculated as Fe$_2$O$_3$ and K$_2$O) wherein both potassium and iron are present on the carrier, 0.1-5 mass % of a silicon compound (calculated as oxide), and 1-5 mass % of a zirconium compound (calculated as oxide). EP 1 308 442 B1 furthermore discloses carrier BET specific surface area in the range of 0.05-10 m$^2$/g, and a water absorption ratio in the range of 10-70%.

US 2009/0177016 A1 discloses a catalyst which comprises a carrier and silver deposited on the carrier in a quantity of at least 10 g/kg, relative to the weight of the catalyst, which carrier has a surface area of at least 1 m$^2$/g, and a pore size distribution such that pores with diameters in the range from 0.2 to 10 µm represent at least 70% of the total pore volume and such pores together provide a pore volume of at least 0.27 ml/g, relative to the weight of the carrier. Table 1 of US 2009/0177016 A1 discloses inventive carriers with surface area in the range of 2.04 to 2.51 m$^2$/g and comparative carrier with surface area of 0.73 m$^2$/g. US 2009/0177016 A1 discloses further in [0124] catalyst compositions using carrier C with surface area of 2.51 m$^2$/g containing 3 mmoles Re and 10.5 mmoles Cs or 2 mmoles Re and 10.3 mmoles Cs per kg of catalyst corresponding to Re-content in the range of 372.4 to 558.6 ppmw and Cs-content of 1369 to 1396 ppmw.

US 2009/0198076 A1 discloses a catalyst for the epoxidation of an olefin to an olefin oxide comprising a support having at least two pore size distributions, each pore size distribution possessing a different mean pore size and a different pore size of maximum concentration, the catalyst further comprising a catalytically effective amount of silver, a promoting amount of rhenium, and a promoting amount of one or more alkali metals, wherein the at least two pore size distributions are within a pore size range of about 0.01 µm to about 50 µm. In a table referring to examples of aluminium oxides US 2009/0198076 A1 discloses supports with surface area in the range of 0.6 to 1.0 m²/g (Support A, B, and C).

US 2010/0191006 A1 discloses a catalyst useful in the epoxidation of an olefin to an olefin oxide, the catalyst comprising a support having a multimodal pore size distribution comprising a first and a second distribution of pore sizes wherein each distribution of pore sizes possesses a different mean pore size and a different pore size of maximum concentration, said support having a catalytically effective amount of silver, a promoting amount of rhenium, and cesium in an amount up to but not exceeding 700 ppm disposed thereon. Table 1 of US 2010/0191006 A1 lists inventive catalysts with Cesium content in the range of 500 to 650 ppm. Re content was selected according to U.S. Pat. No. 4,766,105. US 2010/0191006 A1 further teaches that a catalyst with a Cs content of 750 ppm does not reach the desired productivity.

US 2014/0100379 discloses a carrier comprising at least 85 wt % alpha alumina, at least 0.06 wt % $SiO_2$ and no more than 0.04 wt % $Na_2O$, said carrier comprising a water absorption no greater than 0.35 gram of water/gram of carrier and a ratio of water absorption (gram of water/gram of carrier) to surface area (m² of carrier/gram of carrier) no greater than 0.50 gram of water/m² of carrier. According to US 2014/0100379 the amount of silica could be between 0.06 to 0.4 wt %, and the amount of $Na_2O$ could be between 0.01 and 0.04 wt %, such as 0.02 and 0.03 wt %.

Even though numerous processes for preparing ethylene oxide are disclosed in the state of the art, there is still a need for catalysts with improved performance which can be used to improve processes for preparing ethylene oxide on an industrial scale.

It was an object of the present invention to provide mechanically robust catalysts for the epoxidation of alkenes, which display advantageous activity and/or selectivity. It was a further object of the present invention to provide an improved process for preparing ethylene oxide with good performance over a long period.

According to the present invention, this object is solved by a shaped catalyst body for preparing ethylene oxide, which comprises at least silver, cesium and rhenium applied to an alumina support, wherein the alumina support comprises Si with the Si content in the carrier being defined as $C_{Si}$ and measured in ppm per total support weight, Ca with the Ca content in the carrier being defined as $C_{Ca}$ and measured in ppm per total support weight, and Mg with the Mg content in the carrier being defined as $C_{Mg}$ and measured in ppm per total support weight, wherein the value of the expression $R1=C_{Si}/AW_{Si}-C_{Ca}/AW_{Ca}-C_{Mg}/AW_{Mg}$ is in the range of 1 to 100 mmol/kg, preferably 5 to 75 mmol/kg, more preferable 10 to 60 mmol/kg per weight of the carrier, and $AW_{Si}$, $AW_{Ca}$, and $AW_{Mg}$ relate to atomic weight of Si, Ca and Mg in g/mol, respectively, and wherein the catalyst comprises Ag with the Ag content in the catalyst being defined as $C_{Ag}$ and measured in weight percent per total catalyst weight, Cs with the Cs content in the catalyst being defined as $C_{Cs}$ and measured in ppm per total catalyst weight, Re with the Re content in the catalyst being defined as $C_{Re}$ and measured in ppm per total catalyst weight, wherein the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively and the value of the expression $R3=R2/[R1\times(100-C_{Ag})/100]$ is in the range of 0.05 to 1.

Such catalysts display excellent EO-selectivity, activity and overall ethylene oxide productivity. The present invention further relates to a process for producing the catalyst, to the catalyst obtainable by this process, and to the use of the catalyst for oxidizing ethylene to ethylene oxide. In addition, the present invention relates to a process for production of ethylene oxide from ethylene, which comprises the oxidation of ethylene with oxygen in the presence of said catalyst.

It was surprisingly found that the catalyst according to the present invention with a defined amount of cesium, silver and rhenium applied to an alumina support which has a well defined content of silicium, calcium and magnesium shows excellent activity. Furthermore, the catalyst shows also excellent selectivity after longer time on stream (e.g. TOS≥300 h). Accordingly, novel catalysts for the epoxidation of alkenes have been found, comprising a defined alumina support, the catalyst further comprising silver, rhenium, and cesium, and optionally comprising further lithium, tungsten and sulfur. Such catalysts display excellent ethylene oxide productivity.

According to the present invention, the shaped catalyst body comprises at least silver, cesium and rhenium applied to an alumina support. The alumina support comprises Si with the Si content in the carrier being defined as $C_{Si}$ and measured in ppm per total support weight, Ca with the Ca content in the carrier being defined as $C_{Cs}$ and measured in ppm per total support weight, and Mg with the Mg content in the carrier being defined as $C_{Mg}$ and measured in ppm per total support weight. According to the present invention, the value of the expression $R1=C_{Si}/AW_{Si}-C_{Ca}/AW_{Ca}-C_{Mg}/AW_{Mg}$ is in the range of 1 to 100 mmol/kg, preferably 5 to 75 mmol/kg, more preferable 10 to 60 mmol/kg per weight of the carrier, and $AW_{Si}$, $AW_{Ca}$, and $AW_{Mg}$ relate to atomic weight of Si, Ca and Mg in g/mol, respectively.

Furthermore, the catalyst comprises Ag with the Ag content in the catalyst being defined as $C_{Ag}$ and measured in weight percent per total catalyst weight, Cs with the Cs content in the catalyst being defined as $C_{Cs}$ and measured in ppm per total catalyst weight, Re with the Re content in the catalyst being defined as $C_{Re}$ and measured in ppm per total catalyst weight, and the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively. The catalyst according to the present invention have a defined content of active metals which is linked to the composition of the support. According to the present invention, the value of the expression $R3=R2/[R1\times(100-C_{Ag})/100]$ is in the range of 0.05 to 1.

It was surprisingly found that the content of silica, calcium and magnesium in the support and the relative contents of the active metals is crucial for the properties of the catalyst.

The content of silicon, calcium and magnesium can vary in broad ranges as long as the above relation is fulfilled. Preferably, the silicon content is in the range from 200 to 4000 ppm based on the total weight of the support and calculated as element, more preferably in the range of from 350 to 3500, in particular in the range of from 500 to 3000.

According to a further embodiment, the present invention is also directed to the shaped catalyst body as disclosed above, wherein the Si content in the carrier $C_{Si}$ is in the range from 200 to 4000 ppm based on the total weight of the support and calculated as element.

Preferably, the calcium content is in the range from 100 to 1000 ppm based on the total weight of the support and calculated as element, more preferably in the range of from 250 to 750, in particular in the range of from 400 to 600. According to a further embodiment, the present invention is also directed to the shaped catalyst body as disclosed above, wherein the Ca content in the carrier $C_{Ca}$ is in the range from 100 to 1000 ppm based on the total weight of the support and calculated as element Preferably, the magnesium content is in the range up to 1000 ppm based on the total weight of the support and calculated as element, more preferably in the range of from 10 to 950, in particular in the range of from 50 to 750. According to a further embodiment, the present invention is also directed to the shaped catalyst body as disclosed above, wherein the alumina support comprises up to 1000 ppm of magnesium, based on the total weight of the support and calculated as element.

In the context of the present invention, the catalyst can comprise further active metals. Also the support can comprise further components such as for example sodium or potassium.

According to the present invention, the alumina support preferably has the shape of a hollow cylinder. The precise dimensions of this hollow cylinder are generally of minor importance. However, the hollow cylinders should advantageously have a size which allows unhindered diffusion of the reaction gases at a very large part of the catalytically active external and internal surface coated with silver particles and optionally with further promoters of the alumina supports.

The term "alumina" as used here comprises all conceivable structures such as alpha-, gamma- or theta-alumina. In a preferred embodiment, the alumina support is an alpha-alumina support.

In a further preferred embodiment, the alpha-alumina has a purity of at least 75%, preferably a purity of at least 80%, more preferably a purity of at least 85%, more preferably a purity of at least 90%. For example, the alpha-alumina has a purity of at least 98%, of at least 98.5% or of at least 99%.

The term alpha-alumina therefore also comprises alpha-aluminas which comprise further constituents, in particular constituents selected from the group consisting of zirconium, alkali metals, alkaline earth metals, silicon, zinc, gallium, hafnium, boron, fluorine, copper, nickel, manganese, iron, cerium, titanium, chromium and mixtures of two or more thereof.

The alpha-alumina can comprise the constituents in any suitable form, for example as element or in the form of one or more compounds. If the alpha-alumina comprises one or more constituents in the form of a compound, it comprises the latter as, for example, oxide or mixed oxide.

As regards the amount of the further constituents, the total content of the further constituents is preferably in the range of less than 25% by weight, more preferably less than 20% by weight, more preferably less than 15% by weight and more preferably less than 10% by weight, based on the total weight of the alumina support and calculated as the sum of the elements other than aluminum and oxygen.

If the alumina support comprises, for example, sodium and potassium, it preferably comprises this in an amount in the range of less than 1000 ppm, such as preferably less than 900 ppm by weight, preferably less than 800 ppm by weight, based on the total weight of the alumina support and calculated as element.

If the alumina support comprises, for example, zirconium, it preferably comprises this in an amount in the range of less than 10000 ppm, such as preferably less than 9000 ppm by weight, preferably less than 8000 ppm by weight, based on the total weight of the alumina support and calculated as element.

If the alumina support comprises further constituents, for example constituents selected from the group consisting of gallium, hafnium, boron, fluorine, copper, nickel, manganese, iron, cerium, titanium and chromium, it preferably comprises each of these in an amount of not more than 500 ppm by weight, in each case calculated as metal and based on the total weight of the alumina support.

The alumina supports used according to the invention preferably have a BET surface area determined in accordance with DIN ISO 9277 of from 0.5 to 4.0 $m^2/g$, more preferably in the range from 0.95 to 3.0 $m^2/g$. If not noted otherwise, the BET surface is determined according to DIN ISO 9277 in the context of the present invention.

According to a further embodiment, the present invention is also directed to the shaped catalyst body as disclosed above, wherein the alumina support has a BET surface area in the range from 0.95 to 3.0 $m^2/g$.

According to another embodiment, the present invention is also directed to the shaped catalyst body as disclosed above, wherein the alumina support has a BET surface area in the range from 1.0 to 2.2 $m^2/g$.

Furthermore, the alumina supports according to the invention preferably have pores having diameters in the range from 0.1 to 100 μm, where the pore distribution can be monomodal or polymodal or multimodal, for example bimodal. The alumina supports preferably have a bimodal or multimodal pore distribution.

According to a further embodiment, the present invention is also directed to the shaped catalyst body as disclosed above, wherein the alumina support, preferably the alpha-alumina support, has a bimodal or multimodal pore size distribution.

According to the present invention, at least one of the pore size distributions preferably is within a pore size range of about 0.1 to 5 μm. Furthermore, preferably a further pore size distributions is within a pore size range of about 5 μm to 80 μm, preferably 10 μm to 70 μm, more preferably 33 μm to 60 μm.

Therefore, according to a further embodiment, the present invention is also directed to the shaped catalyst body as disclosed above, wherein the alumina support has at least two pore size distributions wherein at least one of the pore size distributions is within a pore size range of about 0.1 to 5 μm.

According to a further embodiment, the present invention is also directed to the shaped catalyst body as disclosed above, wherein the alumina support has at least two pore size distributions wherein at least one of the pore size distributions is within a pore size range of about 5 μm to 80 μm, preferably 10 μm to 70 μm, more preferably 33 μm to 60 μm According to another embodiment, the present invention is also directed to the shaped catalyst body as disclosed above, wherein the alumina support comprises less than 1% of its total pore volume being present in pores having diameters of less than 0.1 μm.

Unless otherwise noted, the pore size is determined by Hg porosimetry in accordance with DIN 66133 in the context of the present invention.

The water absorption of the alumina supports is preferably in the range from 0.35 ml/g to 0.65 ml/g, preferably in the range from 0.42 ml/g to 0.60 ml/g, determined by vacuum cold water uptake.

In general, such alumina supports are produced by mixing the alumina support material, in particular the alumina, with addition of at least one binder or at least one extrusion aid or at least one pore former or at least one water-comprising composition or a mixture of two or more thereof and subsequently shaping the mixture to give a shaped body.

Suitable pore formers are, for example, cellulose and cellulose derivatives, e.g. carboxymethyl-cellulose, polyolefins such as polyethylenes and polypropylenes. The pore formers are usually removed essentially completely, preferably completely, by means of subsequent calcination of the alumina support.

Suitable binders are, for example, alumina gels with nitric acid or acetic acid, cellulose, methyl-cellulose, ethylcellulose, carboxyethylcellulose, methyl or ethyl stearate, waxes, polyolefin oxides. Suitable extrusion aids are, for example, described in EP 0496 386 B2, page 3 [0019-0021].

The shaped body obtained as described above is usually optionally dried after shaping and calcined to give the alumina support as per (a). Calcination is usually carried out at temperatures in the range from 1200° C. to 1600° C. The alumina support is often additionally washed after calcination in order to remove soluble constituents.

Alumina supports are, for example, commercially available from Saint-Gobain NorPro Co., Noritake Co., CeramTec AG.

The content of the active metals in the catalyst can vary in broad ranges as long as the above definition is fulfilled. Preferably, the rhenium content $C_{Re}$ exceeds 450 ppm per weight of the total catalyst, and the cesium content $C_{Cs}$ exceeds 450 ppm per weight of the total catalyst. Therefore, according to a further embodiment, the present invention is also directed to the shaped catalyst body as disclosed above, comprising rhenium, and cesium, in amounts such that the rhenium content $C_{Re}$ exceeds 450 ppm per weight of the total catalyst, and the cesium content $C_{Cs}$ exceeds 450 ppm per weight of the total catalyst.

Apart from rhenium and cesium, the shaped catalyst body as described above comprises silver as active metal applied to the alumina support. Preferably, the silver content $C_{Ag}$ is in an amount of from 5 to 40% by weight, more preferably in an amount of from 10 to 35% by weight, calculated as element and based on the total weight of the shaped catalyst body The present invention accordingly provides a shaped catalyst body as disclosed above, wherein the shaped catalyst body comprises silver in an amount of from 5 to 40% by weight, based on the total weight of the shaped catalyst body and calculated as element.

The catalyst according to the present invention can comprises further active metals, in particular promoters. According to a further embodiment, the present invention is also directed to the shaped catalyst body as disclosed above, wherein the catalyst comprises at least one promoter selected from the group consisting of elements of groups IA, VIB, VIIB and VIA, preferably selected from the group consisting of tungsten, lithium and sulfur.

Preferably, the catalyst according to the present invention comprises tungsten, lithium and sulfur as active components.

According to a further embodiment, the present invention is also directed to the shaped catalyst body as disclosed above, wherein the shaped catalyst body comprises tungsten in an amount in the range from 5 ppm by weight to 500 ppm by weight, lithium in an amount in the range from 10 ppm by weight to 500 ppm by weight and sulfur in an amount in the range from 0 to 100 ppm by weight, calculated as element and based on the total weight of the shaped catalyst body.

According to another embodiment, the present invention is also directed to the shaped catalyst body as disclosed above, wherein the shaped catalyst body comprises tungsten in an amount in the range from 120 ppm by weight to 250 ppm by weight, lithium in an amount in the range from 120 ppm by weight to 250 ppm by weight and sulfur in an amount in the range from 0 to 50 ppm by weight, calculated as element and based on the total weight of the shaped catalyst body.

The present invention is further directed to a process for producing a shaped catalyst body comprising silver and rhenium applied to an alumina support, which comprises (a) providing an alumina support;
(b) applying silver, cesium and rhenium to the alumina support, wherein for the alumina support, the value of the expression $R1=C_{Si}/AW_{Si}-C_{Ca}/AW_{Ca}-C_{Mg}/AW_{Mg}$ is in the range of 1 to 100 mmol/kg, preferably 5 to 75 mmol/kg, more preferable 10 to 60 mmol/kg weight of the carrier, and $AW_{Si}$, $AW_{Ca}$, and $AW_{Mg}$ relate to atomic weight of Si, Ca and Mg in g/mol, respectively, and wherein the catalyst comprises Ag with the Ag content in the catalyst being defined as $C_{Ag}$ and measured in weight percent per total catalyst weight, Cs with the Cs content in the catalyst being defined as $C_{Cs}$ and measured in ppm per total catalyst weight, Re with the Re content in the catalyst being defined as $C_{Re}$ and measured in ppm per total catalyst weight, wherein the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, and silver, rhenium and caesium are applied in amounts such that the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively and the value of the expression $R3=R2/[R1\times (100-C_{Ag})/100]$ is in the range of 0.05 to 1.

The application of silver to the shaped catalyst body is preferably carried out by bringing the alumina support into contact with at least one mixture G1 comprising at least one silver compound.

As regards the contacting of G1 with the catalyst support, all processes by means of which the mixture can be applied in an appropriate way are generally suitable. The at least one mixture G1 which comprises at least one silver compound is preferably applied by impregnation, spraying or mixing processes to the support. The processes for producing silver catalysts as are disclosed in DE-A 2300512, DE-A 2521906, EP-A 14457, EP-A 85237, EP-A 384312, DE-A 2454972, DE-A 3321895, EP-A 229465, DE-A 3150205, EP-A 172565 and EP-A 357293 may be mentioned by way of example.

The application of silver is particularly preferably effected by vacuum impregnation at room temperature. In the vacuum impregnation, the catalyst support as described above is preferably firstly treated at a pressure in the range of not more than 500 mbar, more preferably at a pressure of not more than 250 mbar and particularly preferably at a pressure of not more than 80 mbar. This is particularly preferably carried out at a temperature in the range from 1° C. to 80° C., more preferably at a temperature in the range from 3° C. to 50° C., more preferably at a temperature in the range from 5° C. to 30° C. and particularly preferably at room temperature. The vacuum treatment is preferably carried out for a time of at least 1 minute, preferably at least 5 minutes, more preferably for a time in the range from 5 minutes to 120 minutes, in particular in the range from 10 minutes to 45 minutes, particularly preferably in the range from 10 minutes to 30 minutes.

After the vacuum treatment, at least mixture G1 is brought into contact with the catalyst support. Mixture G1 is preferably dripped or sprayed on, preferably sprayed on. Application is preferably carried out by means of a nozzle.

Mixture G1 preferably comprises silver in the form of at least one silver compound. The silver compound is preferably applied as a solution, in particular as a solution in water. G1 therefore preferably further comprises at least one solvent, preferably water. To obtain the silver compound in soluble form, a complexing agent such as at least one amine, in particular ethanolamine, EDTA, 1,3- or 1,2-propanediamine, ethylenediamine, and/or an alkali metal oxalate which can simultaneously also act as reducing agent can be additionally added in a suitable manner to the silver compound, for example silver(I) oxide or silver(I) oxalate. In a preferred embodiment, G1 therefore comprises at least one complexing agent, in particular ethanolamine, EDTA, 1,3- or 1,2-propanediamine, ethylenediamine and/or an alkali metal oxalate.

If G1 comprises at least one complexing agent, G1 comprises at least part of the silver in the form of a silver complex. G1 particularly preferably comprises at least part of the silver as a cationic silver-oxalato-ethylenediamine compound. G1 particularly preferably comprises water, silver-oxalato-ethylenediamine complexes and optionally excess ethylenediamine.

As regards the concentration of the silver-comprising compound in G1, this is preferably in the range from 25 to 35%, more preferably in the range from 26 to 32% and more preferably in the range from 27 to 30%.

As indicated above, silver is applied to the alumina support in an amount, calculated as elemental Ag, of from 5 to 40% by weight, more preferably in an amount of from 10 to 30% by weight, calculated as element and based on the total weight of the shaped catalyst body, in step (b).

According to a further embodiment, the present invention is also directed to the process for producing a shaped catalyst body as disclosed above, wherein silver is applied in an amount of from 5 to 40% by weight, based on the total weight of the shaped catalyst body and calculated as element, in (b).

The application in (b) can be carried out in more than one step, for example in 2, 3 or 4 steps. Thus, according to the present invention, for example a mixture G1 and a second mixture G1' can be applied or a mixture G1, a second mixture G1' and a third mixture G1" can be applied. The silver content of the mixture G1, mixture G1' and G1" can vary in the ranges given above and can be identical or different.

The alumina support can optionally be dried and/or calcined between each of the individual steps. If the application according to (b) is carried out in more than one step, the total amount of silver applied to the alumina support after all steps is likewise in the range from 5 to 40% by weight, more preferably in the range from 10 to 35% by weight, calculated as element and based on the total weight of the shaped catalyst body as described above.

The application of the silver can be followed by at least one after-treatment step, for example a drying step, e.g. one, two or more drying steps. Drying is usually carried out at temperatures in the range from 2 to 200° C. The after-treatment step is preferably drying by means of vacuum treatment as described above. This evacuation is preferably carried out at a pressure in the range of not more than 500 mbar, more preferably at a pressure of not more than 250 mbar and particularly preferably at a pressure of not more than 80 mbar. The vacuum treatment is preferably carried out at a temperature in the range from 2 to 50° C., more preferably at a temperature in the range from 5 to 30° C. and particularly preferably at room temperature. The vacuum treatment is carried out for a time of at least 1 minute, preferably at least 5 minutes, more preferably for a time in the range from 5 minutes to 120 minutes, in particular in the range from 10 minutes to 45 minutes, particularly preferably in the range from 10 minutes to 20 minutes.

The application of the silver and optionally the at least one drying step is/are preferably followed by at least one calcination step.

The shaped catalyst body of the invention comprises at least rhenium as promoter in addition to silver. Rhenium is preferably applied to the support by impregnation or spraying or mixing processes as described above for silver.

As regards the point in time at which rhenium is applied, this can be after the application of silver and/or after any of the at least one after-treatment step has been carried out. As an alternative, it is possible to apply the rhenium together with the silver compound or before application of the silver compound to the support. If the rhenium is applied to the alumina support before the silver, at least one after-treatment step, for example a drying step, e.g. one, two or more drying steps, and/or, for example, at least one calcination step can be carried out before the application of silver. Particular preference is given to applying rhenium simultaneously with silver to the alumina support in step (b). According to the present invention rhenium can be applied to the support in parallel to the application of silver, preferably in the form of at least one rhenium compound, in the mixture G1 or separately in a mixture G2.

In case silver is applied in two or more steps using mixtures G1 and G1' and optionally G1", rhenium can be present in mixture G1 or mixture G1' or mixture G1" or in two or more of the mixtures. The rhenium content of the mixtures applied can be identical or different.

The rhenium is particularly preferably applied as a compound, for example as a halide, oxyhalide, oxide or as acid. Furthermore, rhenium can be used in the form of salts of heteropolyacids of rhenium, for example as rhenate or perrhenate, in the production process of the invention.

The present invention therefore also provides a process as described above and a catalyst which is obtainable or obtained by this process comprising (a) providing an alumina support;
(b) applying silver and rhenium to the alumina support by bringing the alumina support into contact with at least one mixture G1 comprising at least one silver compound and at least one rhenium compound, with contacting preferably being carried out by means of vacuum impregnation,
wherein for the alumina support, the value of the expression $R1=C_{Si}/AW_{Si}-C_{Ca}/AW_{Ca}-C_{Mg}/AW_{Mg}$, is in the range of 1 to 100 mmol/kg, preferably 5 to 75 mmol/kg, more preferable 10 to 60 mmol/kg weight of the carrier, and $AW_{Si}$, $AW_{Ca}$, and $AW_{Mg}$ relate to atomic weight of Si, Ca and Mg in g/mol, respectively, and
wherein the catalyst comprises Ag with the Ag content in the catalyst being defined as $C_{Ag}$ and measured in weight percent per total catalyst weight, Cs with the Cs content in the catalyst being defined as $C_{Cs}$ and measured in ppm per total catalyst weight, Re with the Re content in the catalyst being defined as $C_{Re}$ and measured in ppm per total catalyst weight, wherein the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, and rhenium and caesium are applied in amounts such that the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively and the value of the expression $R3=R2/[R1\times(100-C_{Ag})/100]$ is in the range of 0.05 to 1.

The present invention therefore also provides a process as described above and a catalyst which is obtainable or obtained by this process comprising (a) providing an alumina support,
(b) applying silver and rhenium to the alumina support by
(b1) bringing the alumina support into contact with at least one mixture G1 comprising at least one silver compound, and
(b2) bringing the alumina support into contact with at least one mixture G1' comprising at least one silver compound and at least one rhenium compound with contacting preferably being carried out by means of vacuum impregnation, wherein for the alumina support, the value of the expression $R1=C_{Si}/AW_{Si}-C_{Cd}/AW_{Ca}-C_{Mg}/AW_{Mg}$ is in the range of 1 to 100 mmol/kg, preferably 5 to 75 mmol/kg, more preferable 10 to 60 mmol/kg per weight of the carrier, and $AW_{Si}$, $AW_{Ca}$, and $AW_{Mg}$ relate to atomic weight of Si, Ca and Mg in g/mol, respectively, and wherein the catalyst comprises Ag with the Ag content in the catalyst being defined as $C_{Ag}$ and measured in weight percent per total catalyst weight, Cs with the Cs content in the catalyst being defined as $C_{Cs}$ and measured in ppm per total catalyst weight, Re with the Re content in the catalyst being defined as $C_{Re}$ and measured in ppm per total catalyst weight, wherein the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, and rhenium and caesium are applied in amounts such that the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively and the value of the expression $R3=R2/[R1\times(100-C_{Ag})/100]$ is in the range of 0.05 to 1.

The process might comprise further steps such as drying and/or calcination steps. It is also possible that the process comprises drying and/or calcination steps after step (b1) and (b2). In step b), rhenium is preferably applied as a compound to the alumina support, with the compound being selected from the group consisting of ammonium perrhenate, rhenium (III) chloride, rhenium (V) chloride, rhenium (V) fluoride, rhenium (VI) oxide and rhenium (VII) oxide. For the purposes of the invention, rhenium is particularly preferably applied as ammonium perrhenate to the alumina support.

Apart from rhenium, the shaped catalyst body can comprise at least one further promoter. The shaped catalyst body particularly preferably comprises at least one further promoter.

The invention therefore comprises, for example, embodiments in which the shaped catalyst body comprises five different promoters, four different promoters, three different promoters, two different promoters or one further promoter applied in addition to rhenium to the alumina support. In particular, this at least one further promoter is selected from among elements of groups IA, VIB, VIIB and VIA of the Periodic Table of the Elements, particularly preferably selected from the group consisting of tungsten, lithium, sulfur, cesium, chromium, manganese, molybdenum and potassium.

The present invention accordingly provides a shaped catalyst body as described above and a process for producing a shaped catalyst body as described above and also a shaped catalyst body which is obtainable or obtained by this process, wherein the shaped catalyst body comprises at least one further promoter selected from the group consisting of elements of groups IA, VIB, VIIB and VIA, preferably selected from the group consisting of tungsten, lithium and sulfur.

In a particularly preferred embodiment, the catalyst comprises at least lithium, tungsten and sulfur as promoters in addition to cesium and rhenium.

If the shaped catalyst body comprises at least one further promoter, it preferably comprises a total amount of these further promoters in an amount of from 10 ppm by weight to 3000 ppm by weight, preferably in an amount of from 10 to 2500 ppm, more preferably in each case in an amount of from 50 ppm by weight to 2000 ppm by weight and particularly preferably in each case in an amount of from 80 ppm by weight to 1500 ppm by weight, based on the total weight of the shaped catalyst body and calculated as sum of the elements.

If the shaped catalyst body comprises tungsten as promoter, as described above, the tungsten is preferably applied as tungsten compound to the support. Here, it is in principle possible to use any suitable tungsten compound. Preference is given to applying tungsten in the form of tungstate or tungstic acid. The shaped catalyst body preferably comprises tungsten as promoter in an amount of up to 800 ppm by weight, preferably in an amount in the range from 5 to 500 ppm by weight, more preferably in an amount in the range from 100 to 300 ppm by weight, based on the total weight of the shaped catalyst body and calculated as element.

If the shaped catalyst body comprises lithium as promoter as described above, the lithium is preferably applied as lithium compound to the support. Here, it is in principle possible to use any suitable lithium compound. Lithium is preferably applied in the form of lithium nitrate. If the shaped catalyst body comprises lithium as promoter, it preferably comprises lithium in an amount of up to 700 ppm by weight, preferably in an amount in the range from up to 10 ppm by weight to 500 ppm by weight, more preferably in an amount in the range from 80 ppm by weight to 250 ppm by weight, based on the total weight of the shaped catalyst body and calculated as element.

If the shaped catalyst body comprises sulfur as promoter as described above, the sulfur is preferably applied as a sulfur compound to the support. Here, it is in principle possible to use any suitable sulfur compound. Sulfur is preferably applied in the form of ammonium sulfate. If the shaped catalyst body comprises sulfur as promoter, it preferably comprises sulfur in an amount of from 0 to 100 ppm by weight, more preferably in an amount in the range from 1 ppm by weight to 50 ppm by weight, based on the total weight of the shaped catalyst body and calculated as element.

The present invention accordingly provides a shaped catalyst body as described above and a process for producing a shaped catalyst body as described above and also a shaped catalyst body which is obtainable or obtained by this process.

If the shaped catalyst body comprises at least one further promoter, this at least one further promoter is preferably applied in the form of compounds, for example in the form of complexes or in the form of salts, for example in the form of halides, for example in the form of fluorides, bromides or chlorides, or in the form of carboxylates, nitrates, sulfates or sulfides, phosphates, cyanides, hydroxides, carbonates or as salts of heteropolyacids, to the support in the process of the invention for producing the catalyst.

The at least one further promoter, more preferably the at least one further promoter compound, is preferably dissolved in a suitable solution, preferably in water, before application. The alumina support is then preferably brought into contact (impregnated) with the resulting solution comprising one or more of the further promoters.

If a plurality of further promoters are to be added, these can be applied to the support either together or separately in one step or in a plurality of steps. As regards the solution comprising one or more of the further promoters, this can be produced in any suitable way. For example, the promoters can each be dissolved separately in one solution each and the resulting solutions each comprising one promoter can subsequently be used for impregnation. It is likewise possible for two or more of the further promoters to be dissolved together in one solution and the resultant solution to be used subsequently for the impregnation. In addition, it is possible for the resulting solutions comprising at least one promoter to be combined before impregnation and the resulting solution comprising all promoters to be applied to the support.

As regards the point in time at which the at least one further promoter is applied, the application can be carried out after the application of silver and/or rhenium and/or after at least one optional after-treatment step has been carried out. As an alternative, it is possible to apply the at least one further promoter together with the silver compound and/or the rhenium compound or before the silver compound and/or the rhenium compound to the support.

Particular preference is given to applying the at least one further promoter simultaneously with silver and rhenium to the alumina support in step (b). Here, the at least one further promoter can be applied in parallel to the application of silver and rhenium, in a separate mixture G3 to the support.

The at least one further promoter is preferably applied as constituent of the mixture G1, which preferably comprises rhenium and/or at least one rhenium compound in addition to the at least one silver compound, to the alumina support. The at least one further promoter is accordingly preferably applied together with rhenium and silver to the alumina support.

Particular preference is given to all further promoters comprised in the shaped catalyst body being applied together with rhenium and silver to the alumina support.

If, for example, at least cesium, tungsten, lithium, sulfur are used as further promoters, a particularly preferred embodiment comprises producing at least one solution comprising cesium (in the form of at least one compound) and tungsten (in the form of at least one compound), a further solution comprising lithium (in the form of at least one compound) and sulfur (in the form of at least one compound) and a further solution comprising rhenium (in the form of at least one compound).

In one embodiment, the solutions are applied to the support in separate impregnation steps. Particular preference is given to combining the solutions with a solution comprising at least one silver compound to give the mixture G1. Thus, G1 particularly preferably comprises in addition to the at least one silver compound, at least one rhenium compound, at least one cesium compound, at least one lithium compound, at least one tungsten compound and optionally further promoters, in each case in the form of at least one compound.

The present invention accordingly provides a shaped catalyst body as described above and a process for producing a shaped catalyst body as described above and also a shaped catalyst body which is obtainable or obtained by this process, where the catalyst additionally comprises at least one further promoter selected from among elements of groups IA, VIB, VIIB and VIA of the Periodic Table of the Elements, preferably selected from the group consisting of tungsten, lithium, sulfur, chromium, manganese, molybdenum and potassium, and the at least one further promoter is preferably applied to the alumina support by bringing the alumina support into contact, preferably by means of vacuum impregnation, with the mixture G1 which additionally comprises the at least one promoter, in step (b).

In a particularly preferred embodiment, the catalyst comprises tungsten in an amount of from 100 ppm by weight to 500 ppm by weight, lithium in an amount of from 10 ppm by weight to 500 ppm by weight and sulfur in an amount of from 0 to 50 ppm by weight.

The present invention accordingly provides a shaped catalyst body as described above and a process for producing a shaped catalyst body as described above and also a shaped catalyst body which is obtainable or obtained by this process, where the shaped catalyst body comprises tungsten in an amount of from 100 ppm by weight to 500 ppm by weight, lithium in an amount of from 10 ppm by weight to 500 ppm by weight and sulfur in an amount of from 0 to 50 ppm by weight.

Step (b) can be followed by at least one after-treatment step, for example a drying step, e.g. one, two or more drying steps. Drying is usually carried out at temperatures in the range from 2 to 200° C. For example, the after-treatment step is drying by means of vacuum treatment as described above. This evacuation is preferably carried out at a pressure in the range of not more than 500 mbar, more preferably at a pressure of not more than 250 mbar and particularly preferably at a pressure of not more than 80 mbar. The vacuum treatment is preferably carried out at a temperature in the range from 2° C. to 50° C., more preferably at a temperature in the range from 5° C. to 30° C. and particularly preferably at room temperature. The vacuum treatment is carried out for a time of at least 1 minute, preferably at least 5 minutes, more preferably for a time in the range from 5 minutes to 120 minutes, in particular in the range from 10 minutes to 45 minutes, particularly preferably in the range from 10 minutes to 20 minutes.

The optionally dried alumina support according to (b) is preferably calcined. According to a further embodiment, the present invention is also directed to the process for producing a shaped catalyst body as disclosed above, wherein the process further comprises (c) calcining the alumina support obtained according to (b).

If a calcination is carried out in step (c), this calcination is preferably carried out at temperatures in the range from 150 to 750° C., preferably in the range from 200 to 500° C. and particularly preferably in the range from 220 to 350° C., with the calcination time generally being at least 5 minutes or more, for example in the range from 5 minutes to 24 hours or in the range from 10 minutes to 12 hours.

The calcination time is particularly preferably in the range from 5 minutes to 3 hours. The calcination can be carried out at a constant temperature, but embodiments in which the temperature is changed continuously or discontinuously during the calcination time are also comprised.

The calcination can be carried out under any gas atmosphere suitable for this purpose, for example in an inert gas or a mixture of an inert gas and from 10 ppm to 21% by volume of oxygen. As inert gas, mention may be made by way of example of nitrogen, argon, carbon dioxide, helium and combinations of at least two of the abovementioned inert gases. If the calcination is carried out in an inert gas, particular preference is given to nitrogen. In an alternative preferred embodiment, air and/or lean air is used.

Furthermore, the calcination is preferably carried out in a muffle furnace, convection oven, in a rotary furnace and/or a belt calcination furnace.

The present invention is also directed to a shaped catalyst body obtainable or obtained by a process according to the process as disclosed above.

The shaped catalyst bodies of the invention or the shaped catalyst bodies which are obtainable or obtained by a process according to the invention are particularly suitable as catalysts for preparing ethylene oxide from ethylene in a process comprising oxidation of ethylene. High selectivities, in particular advantageous initial selectivities, and good activities are achieved.

The present invention therefore also provides, according to a further aspect, a process for preparing ethylene oxide from ethylene, which comprises oxidation of ethylene in the presence of a shaped catalyst body for the preparation of ethylene oxide as described above.

The present invention is also directed to a process for preparing ethylene oxide by gas-phase oxidation of ethylene by means of oxygen in the presence of a shaped catalyst body as disclosed above or a shaped catalyst body obtained or obtainable according to the process of the present invention.

In addition, the present invention also provides for the use of a shaped catalyst body as described above for preparing ethylene oxide by gas-phase oxidation of ethylene.

According to the invention, the epoxidation can be carried out by all processes known to those skilled in the art. It is possible to use all reactors which can be used in the ethylene oxide production processes of the prior art; for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987) or reactors having a loose catalyst bed and cooling tubes, for example the reactors described in DE-A 3414717, EP 0082609 and EP-A 0339748. The epoxidation is preferably carried out in at least one tube reactor, preferably in a shell-and-tube reactor. To prepare ethylene oxide from ethylene and oxygen, it is possible according to the invention to carry out the reaction under conventional reaction conditions as described, for example, in DE-A 2521906, EP-A 0 014 457, DE-A 2300512, EP-A 0 172 565, DE-A 2454972, EP-A 0 357 293, EP-A 0 266 015, EP-A 0 085 237, EP-A 0 082 609 and EP-A 0 339 748. Inert gases such as nitrogen or gases which are inert under the reaction conditions, e.g. steam, methane, and also optionally reaction moderators, for example halogenated hydrocarbons such as ethyl chloride, vinyl chloride or 1,2-dichloroethane can additionally be mixed into the reaction gas comprising ethylene and molecular oxygen. The oxygen content of the reaction gas is advantageously in a range in which no explosive gas mixtures are present. A suitable composition of the reaction gas for preparing ethylene oxide can, for example, comprise an amount of ethylene in the range from 10 to 80% by volume, preferably from 20 to 60% by volume, more preferably from 25 to 50% by volume and particularly preferably in the range from 25 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7.5% by volume, based on the total volume of the reaction gas.

The reaction gas preferably comprises a chlorine-comprising reaction moderator such as ethyl chloride, vinyl chloride or dichloroethane in an amount of from 0 to 15 ppm by weight, preferably in an amount of from 0.1 to 8 ppm by weight. The remainder of the reaction gas generally comprises hydrocarbons such as methane and also inert gases such as nitrogen. In addition, other materials such as steam, carbon dioxide or noble gases can also be comprised in the reaction gas.

The above-described constituents of the reaction mixture may optionally each have small amounts of impurities. Ethylene can, for example, be used in any degree of purity suitable for the gas-phase oxidation according to the invention. Suitable degrees of purity include, but are not limited to, "polymer-grade" ethylene which typically has a purity of at least 99% and "chemical-grade" ethylene which typically has a purity of less than 95%. The impurities typically comprise, in particular, ethane, propane and/or propene.

The reaction or oxidation of ethylene to ethylene oxide is usually carried out at elevated temperature. Preference is given to temperatures in the range from 150 to 350° C., more preferably in the range from 180 to 300° C., more preferably temperatures in the range from 190° C. to 280° C. and particularly preferably temperatures in the range from 200° C. to 280° C. The present invention therefore also provides a process as described above in which the oxidation is carried out at a temperature in the range 180-300° C., preferably in the range from 200 to 280° C.

The reaction according to the invention (oxidation) is preferably carried out at pressures in the range from 5 bar to 30 bar. The oxidation is more preferably carried out at a pressure in the range from 5 bar to 25 bar, preferably at a pressure in the range from 10 bar to 20 bar and in particular in the range from 14 bar to 20 bar. The present invention therefore also provides a process as described above in which the oxidation is carried out at a pressure in the range from 14 bar to 20 bar.

The oxidation is preferably carried out in a continuous process. If the reaction is carried out continuously, the GHSV (gas hourly space velocity) is, depending on the type of reactor chosen, for example on the size/cross-sectional area of the reactor, the shape and size of the catalyst, preferably in the range from 800 to 10 000/h, preferably in the range from 2000 to 6000/h, more preferably in the range from 2500 to 5000/h, where the values indicated are based on the volume of the catalyst.

According to a further embodiment, the present invention is also directed to a process for preparing ethylene oxide by gas-phase oxidation of ethylene by means of oxygen as disclosed above, wherein the work rate of ethylene oxide production measured at greater than 180 $kg_{EO}/m^3_{Cat}h$, preferably to a work rate of greater than 200 $kg_{EO}m^3_{Cat}h$.

The preparation of ethylene oxide from ethylene and oxygen can advantageously be carried out in a recycle process. Here, the reaction mixture is circulated through the reactor with the newly formed ethylene oxide and also the by-products formed in the reaction being removed from the product gas stream after each pass and the product gas stream being, after having been supplemented with the required amounts of ethylene, oxygen and reaction moderators, reintroduced into the reactor. The separation of the ethylene oxide from the product gas stream and its work-up can be carried out by customary methods of the prior art (cf. Ullmann's Encyclopedia of Industrial Chemistry, 5th edition, vol. A-10, pp. 117-135, 123-125, VCH-Verlagsgesellschaft, Weinheim 1987).

The present invention is also directed to the use of a shaped catalyst body as disclosed above or a shaped catalyst body obtained or obtainable according to the process of the present invention as catalyst for preparing ethylene oxide by gas-phase oxidation of ethylene by means of oxygen.

The present invention includes the following embodiments, wherein these include the specific combinations of embodiments as indicated by the respective interdependencies defined therein.

1. A shaped catalyst body for preparing ethylene oxide, which comprises at least silver, cesium and rhenium applied to an alumina support, wherein the alumina support comprises Si with the Si content in the carrier being defined as $C_{Si}$ and measured in ppm per total support weight, Ca with the Ca content in the carrier being defined as Cc, and measured in ppm per total support weight, and Mg with the Mg content in the carrier being defined as $C_{Mg}$ and measured in ppm per total support weight,
   wherein the value of the expression $R1=C_{Si}/AW_{Si}-C_{Ca}/AW_{Ca}-C_{Mg}/AW_{Mg}$ is in the range of 1 to 100 mmol/kg, preferably 5 to 75 mmol/kg, more preferable 10 to 60 mmol/kg per weight of the carrier, and $AW_{Si}$, $AW_{Ca}$, and $AW_{Mg}$ relate to atomic weight of Si, Ca and Mg in g/mol, respectively, and
   wherein the catalyst comprises Ag with the Ag content in the catalyst being defined as $C_{Ag}$ and measured in weight percent per total catalyst weight, Cs with the Cs content in the catalyst being defined as $C_{Cs}$ and measured in ppm per total catalyst weight, Re with the Re content in the catalyst being defined as $C_{Re}$ and measured in ppm per total catalyst weight,
   wherein the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively and
   the value of the expression $R3=R2/[R1\times(100-C_{Ag})/100]$ is in the range of 0.05 to 1.
2. The shaped catalyst body according to embodiment 1, wherein the Si content in the carrier $C_{Si}$ is in the range from 200 to 4000 ppm based on the total weight of the support and calculated as element.
3. The shaped catalyst body according to embodiment 1 to 2, wherein the Ca content in the carrier $C_{Ca}$ is in the range from 100 to 1000 ppm based on the total weight of the support and calculated as element.
4. The shaped catalyst body according to embodiment 1 or 3, wherein the alumina support comprises up to 1000 ppm of magnesium, based on the total weight of the support and calculated as element.
5. The shaped catalyst body according to any of embodiments 1 to 4, comprising rhenium, and cesium, in amounts such that the rhenium content $C_{Re}$ exceeds 450 ppm per weight of the total catalyst, and the cesium content $C_{Cs}$ exceeds 450 ppm per weight of the total catalyst.
6. The shaped catalyst body according to any of embodiments 1 to 5, wherein the alumina support has a BET surface area in the range from 0.95 to 3.0 m²/g.
7. The shaped catalyst body according to any of embodiments 1 to 6, wherein the alumina support has at least two pore size distributions wherein at least one of the pore size distributions is within a pore size range of about 0.1 to 5 µm.
8. The shaped catalyst body according to any of embodiments 1 to 7, wherein the shaped catalyst body comprises silver in an amount of from 5 to 40% by weight, based on the total weight of the shaped catalyst body and calculated as element.
9. The shaped catalyst body according to any of embodiments 1 to 8, wherein the catalyst comprises at least one promoter selected from the group consisting of elements of groups IA, VIB, VIIB and VIA, preferably selected from the group consisting of tungsten, lithium and sulfur.
10. A process for producing a shaped catalyst body comprising silver and rhenium applied to an alumina support, which comprises
    (a) providing an alumina support;
    (b) applying silver, cesium and rhenium to the alumina support,
    wherein for the alumina support, the value of the expression $R1=C_{Si}/AW_{Si}-C_{Ca}/AW_{Ca}-C_{Mg}/AW_{Mg}$ is in the range of 1 to 100 mmol/kg, preferably 5 to 75 mmol/kg, more preferable 10 to 60 mmol/kg per weight of the carrier, and $AW_{Si}$, $AW_{Ca}$, and $AW_{Mg}$ relate to atomic weight of Si, Ca and Mg in g/mol, respectively, and
    wherein for the catalyst, the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol,
    and rhenium and caesium are applied in amounts such that the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively and the value of the expression $R3=R2/[R1\times(100-C_{Ag})/100]$ is in the range of 0.05 to 1.
11. The process according to embodiment 10, wherein the process further comprises (c) calcining the alumina support obtained according to (b).
12. The process according to embodiment 10 or 11, wherein silver is applied in an amount of from 5 to 35% by weight, based on the total weight of the shaped catalyst body and calculated as element, in (b).
13. A shaped catalyst body obtainable or obtained by a process according to any of embodiments 10 to 12.
14. A process for preparing ethylene oxide by gas-phase oxidation of ethylene by means of oxygen in the presence of a shaped catalyst body according to any of embodiments 1 to 9 or 13.
15. The use of a shaped catalyst body according to any of embodiments 1 to 9 or 13 as catalyst for preparing ethylene oxide by gas-phase oxidation of ethylene by means of oxygen.

BRIEF DESCRIPTION OF THE FIGURES

FIG. 1 shows testing data of the inventive catalyst 3.2.2.16 (white markers) and of the comparative catalyst 3.2.2.15 (black markers). On the x-axis, the time on stream in [hours] is plotted. On the left y-axis, selectivity is plotted in [%]. On the right y-axis, coolant temperature is plotted in [° C.].

Examples will be used below to illustrate the invention.

EXAMPLES

1. Characterization Methods
1.1 Analysis of Total Amount of Ca-, Mg-, and Si-Impurities in Alumina Carriers
1.1.1 Sample Preparation for Measurement of Ca, Mg, and Si Approximately 100-200 mg (at an error margin of ±0.1 mg) of the aluminum oxide carrier sample were weighted into a platinum crucible. 1.0 g of lithium metaborate (LiBO$_2$) was added. The mixture was melted in an automated fusion apparatus with a temperature ramp up to max. 1150° C.

After cooling down, the melt was dissolved in deionized water by careful heating. Then, 10 ml of semi-concentrated hydrochloric acid (concentrated HCl diluted with deionized water, volume ratio 1:1 corresponds to about 6M) was added. Finally, the solution was filled up to a volume of 100 ml with deionized water.
1.1.2 Measurement of Ca, Mg, and Si Ca, Mg, and Si from the sample solution 1.1.1 were determined by Inductively Coupled Plasma-Optical Emission Spectroscopy (ICP-OES).

Apparatus: ICP-OES Varian Vista Pro
Parameters:
    Wavelengths [nm]: Ca 317.933
      Mg 285.213
      Si 251.611
    Integration time: 10 s
    Nebulizer: Conikal 3 ml
    Nebulizer pressure: 270 kPa
    Pump rate: 30 rpm
    Calibration: external (matrix-matched standards)
2. Carriers Si-, Ca- and Mg-content [ppm] per total weight of the carrier and carrier BET surface area are summarized in Table 1.

TABLE 1

Total Si-, Ca-, and Mg-content [ppm] per weight carrier and carrier BET-surface area [m$^2$/g]

|  | A | B | C | D | E |
| --- | --- | --- | --- | --- | --- |
| Si-content [ppm] | 900 | 900 | 700 | 800 | 700 |
| Ca-content [ppm] | 300 | 300 | 200 | 300 | 300 |
| Mg-content [ppm] | 200 | 100 | 100 | 200 | 100 |
| BET surface area [m$^2$/g] | 0.88 | 0.91 | 1.12 | 1.29 | 1.37 |

|  | F | G | H | I | J |
| --- | --- | --- | --- | --- | --- |
| Si-content [ppm] | 900 | 700 | 2300 | 2400 | 700 |
| Ca-content [ppm] | 300 | 300 | 400 | 400 | 300 |
| Mg-content [ppm] | 200 | 100 | 400 | 500 | 100 |
| BET surface area [m$^2$/g] | 1.41 | 1.57 | 1.42 | 1.84 | 1.06 |

3. Preparation of Catalysts
3.1 Production of the Silver Complex Solution 550 g of silver nitrate were completely dissolved in 1.5 l of water under constant stirring and the solution was warmed to 40° C. 402 g of KOH (47.8%) was mixed with 1.29 L water. A separate solution of 216.3 g oxalic acid was added to the KOH solution, which was then warmed to 40° C. The potassium oxalate solution was then added to the silver nitrate solution within 45 min (volume flow rate ca. 33 ml/min) with the aid of a dosing pump and the solution was stirred for approximately 1 h at 40° C. The precipitated silver oxalate was then filtered and the obtained filter cake was washed with 1 L water portions until the filter cake was free of potassium and nitrate (ca. 10 l total). The water was removed from the filter cake by flowing air through the filter apparatus and the water content of the filter cake was measured. Typically a cake of 620 g with a water content of 20.8% was obtained.

Ethylenediamine (306 g) was cooled in an ice bath to ca. 10° C. and 245 g water was added in small portions. At the end of the water addition, 484.7 g of the (still damp) silver oxalate was added to the ethylenediamine/water mixture within 30 minutes. The mixture was stirred at room temperature overnight and any undissolved material removed via centrifugation. The silver content was determined refractometrically and the density was measured.

The obtained solution contained 28.0-29.3 weight % silver and had a density of 1.512-1.532 g/mL.
3.2. Preparation of Ag Containing Catalysts with an Ag Content of >20 wt.-% (Double Impregnation)
3.2.1 Preparation of Ag-Containing Intermediate Products An amount of carrier A-D listed in Table 2 was placed into a 2 L glass flask. The flask was attached to a rotary evaporator which was set under vacuum pressure of 30 mbar. The rotary evaporator system was set in rotation of 30 rpm. An amount of the silver complex solution listed in Table 2 was added onto the carrier A-D over 15 minutes under vacuum of 30 mbar. After addition of the silver complex solution, the rotary evaporator system was continued to rotate under vacuum for another 15 minutes. The impregnated carrier was then left in the apparatus at room temperature and atmospheric pressure for 1 hour and mixed gently every 15 minutes.

The impregnated carrier was calcined for 12 minutes at 290° C. under 23 m$^3$/h flowing nitrogen in a calcination oven to yield a Ag-containing intermediate products.

TABLE 2

Carrier name and amounts of ingredients used for preparation of Ag-containing intermediate products 3.2.1.1-3.2.1.4.

|  | Intermediate 3.2.1.1 | Intermediate 3.2.1.2 | Intermediate 3.2.1.3 | Intermediate 3.2.1.4 |
| --- | --- | --- | --- | --- |
| Carrier name | Carrier A | Carrier B | Carrier C | Carrier D |
| Amount of carrier [g] | 173.6 | 173.9 | 173.6 | 348.4 |
| Amount of Ag-complex solution [g] | 115.9838 | 115.7641 | 114.5389 | 227.7935 |
| Ag-content in Ag-complex solution [wt %] | 28.93 | 29.04 | 29.3 | 28.7 |
| Ag-content in Ag-containing intermediate [wt %] | 16.2 | 16.2 | 16.2 | 15.8 |

3.2.2. Preparation of Final Catalysts

An amount of Ag-containing intermediate products 3.2.1.1-3.2.1.4 listed in Table 3 were placed into a 2 L glass flask. The flask was attached to a rotary evaporator which was set under vacuum pressure of 30 mbar. The rotary evaporator system was set in rotation of 30 rpm. An amount of the silver complex solution listed in Table 3 prepared according to step 3.1 was mixed with an amount of promoter solution I listed in Table 3, an amount of promoter solution II listed in Table 3, an amount of promoter solution III listed in Table 3. Promoter solution I was made from dissolving lithium nitrate (FMC, 99.3%) and ammonium sulfate (Merck, 99.4%) in DI water to achieve target Li and S contents listed in Table 3. Promoter solution II was made from dissolving tungstic acid (HC Starck, 99.99%) in DI water and cesium hydroxide in water (HC Starck, 50.42%) to achieve target Cs and W contents listed in Table 3. Promoter solution III was made from dissolving ammonium perrhenate (Engelhard, 99.4%) in DI water to achieve target Re content listed in Table 3. The combined solution containing silver complex solution, promoter solutions I, II, and III was stirred for 5 minutes. The combined solution was added onto the silver-containing intermediate products 3.2.1.1-3.2.1.4 over 15 minutes under vacuum of 30 mbar. After addition of the combined solution, the rotary evaporator system was continued to rotate under vacuum for another 15 minutes. The impregnated carrier was then left in the apparatus at room temperature and atmospheric pressure for 1 hour and mixed gently every 15 minutes.

The impregnated material was calcined for 10 minutes at 290° C. under 23 m$^3$/h flowing nitrogen in a calcination oven to yield the final catalysts.

TABLE 3

Intermediate name and amounts of ingredients used for preparation of catalysts 3.2.2.1-3.2.2.4.

|  | Catalyst 3.2.2.1 (comparative) | Catalyst 3.2.2.2 (comparative) | Catalyst 3.2.2.3 (inventive) | Catalyst 3.2.2.4 (inventive) |
|---|---|---|---|---|
| Ag-containing Intermediate from Table 2 | 3.2.1.1 | 3.2.1.2 | 3.2.1.3 | 3.2.1.4 |
| Amount of Ag-containing Intermediate [g] | 205.2 | 205.1 | 204.0 | 207.6 |
| Amount of Ag-complex solution [g] | 96.9312 | 95.8464 | 92.1530 | 89.5818 |
| Ag-content in Ag-complex solution [wt %] | 28.0 | 28.3 | 29.3 | 28.7 |
| Amount of promoter solution I [g] | 1.5505 | 1.5501 | 1.5425 | 1.5582 |
| Li-/S-content in promoter solution I [wt %] | 2.85/0.21 | 2.85/0.21 | 2.85/0.21 | 2.85/0.21 |
| Amount of promoter solution II [g] | 2.3257 | 2.3251 | 2.3137 | 2.3373 |
| Cs-/W-content in promoter solution II [wt %] | 4.0/2.0 | 4.0/2.0 | 6.0/2.0 | 7.0/1.9 |
| Amount of promoter solution III [g] | 2.2122 | 2.2117 | 3.3295 | 4.3587 |
| Re-content in promoter solution III [wt %] | 4.1 | 4.1 | 4.1 | 3.7 |

Further Catalysts were prepared similar to catalysts 3.2.2.1-3.2.2.4.

Catalyst compositions are listed in Table 4.

TABLE 4

Catalyst compositions (Ag-contents are reported in percent by weight of total catalyst, dopant values are reported in parts per million by weight of total catalyst)

| Example | Carrier | Ag [wt-%] | Li [ppm] | S [ppm] | W [ppm] | Cs [ppm] | Re [ppm] |
|---|---|---|---|---|---|---|---|
| 3.2.2.1 (comparative) | A | 26.0 | 190 | 14 | 200 | 400 | 390 |
| 3.2.2.2 (comparative) | B | 26.0 | 190 | 14 | 200 | 400 | 390 |
| 3.2.2.3 (inventive) | C | 26.0 | 190 | 14 | 200 | 600 | 590 |
| 3.2.2.4 (inventive) | D | 25.0 | 190 | 14 | 190 | 700 | 690 |
| 3.2.2.5 (inventive) | E | 26.0 | 190 | 14 | 200 | 700 | 690 |
| 3.2.2.6 (inventive) | F | 25.0 | 190 | 14 | 190 | 700 | 690 |
| 3.2.2.7 (inventive) | G | 26.0 | 190 | 14 | 200 | 800 | 780 |
| 3.2.2.8 (inventive) | G | 26.0 | 190 | 14 | 200 | 700 | 690 |
| 3.2.2.9 (inventive) | G | 26.0 | 190 | 14 | 200 | 900 | 870 |

TABLE 4-continued

Catalyst compositions (Ag-contents are reported in percent by weight of total catalyst, dopant values are reported in parts per million by weight of total catalyst)

| Example | Carrier | Ag [wt-%] | Li [ppm] | S [ppm] | W [ppm] | Cs [ppm] | Re [ppm] |
|---|---|---|---|---|---|---|---|
| 3.2.2.10 (comparative) | G | 26.0 | 190 | 14 | 200 | 700 | 870 |
| 3.2.2.11 (comparative) | H | 26.0 | 190 | 14 | 200 | 600 | 590 |
| 3.2.2.12 (comparative) | H | 26.0 | 190 | 14 | 200 | 700 | 690 |
| 3.2.2.13 (comparative) | H | 26.0 | 190 | 14 | 200 | 500 | 690 |
| 3.2.2.14 (inventive) | H | 26.0 | 190 | 14 | 200 | 700 | 490 |
| 3.2.2.15 (comparative) | H | 26.0 | 190 | 14 | 200 | 600 | 590 |
| 3.2.2.16 (inventive) | H | 26.0 | 190 | 14 | 200 | 700 | 490 |
| 3.2.2.17 (comparative) | I | 26.0 | 190 | 14 | 200 | 700 | 690 |
| 3.2.2.18 (inventive) | I | 26.0 | 190 | 14 | 200 | 1000 | 690 |
| 3.2.2.19 (comparative) | I | 26.0 | 190 | 14 | 200 | 1300 | 690 |
| 3.2.2.20 (comparative) | I | 26.0 | 190 | 14 | 200 | 800 | 780 |
| 3.2.2.21 (inventive) | I | 26.0 | 190 | 14 | 200 | 1130 | 780 |
| 3.2.2.22 (comparative) | I | 26.0 | 190 | 14 | 200 | 1470 | 780 |

TABLE 5

Key catalyst properties with respect to claims

| Example | Carrier BET surface area [m²/g] | Carrier $C_{Si}$ [ppm] | Carrier $C_{Ca}$ [ppm] | Carrier $C_{Mg}$ [ppm] | Carrier R1 [mmol/kg] | Catalyst Ag-content [wt %] | Catalyst Cs-content [ppm] | Catalyst Re-content [ppm] | Catalyst R2 [mmol/kg] | Catalyst R3 |
|---|---|---|---|---|---|---|---|---|---|---|
| 3.2.2.1) comparative | 0.88 | 900 | 300 | 200 | 16.33 | 26.0 | 400 | 390 | 0.915 | 0.076 |
| 3.2.2.2 comparative | 0.91 | 900 | 300 | 100 | 20.45 | 26.0 | 400 | 390 | 0.915 | 0.060 |
| 3.2.2.3 inventive | 1.12 | 700 | 200 | 100 | 15.82 | 26.0 | 600 | 590 | 1.346 | 0.115 |
| 3.2.2.4 inventive | 1.29 | 800 | 300 | 200 | 12.77 | 25.0 | 700 | 690 | 1.561 | 0.163 |
| 3.2.2.5 inventive | 1.37 | 700 | 300 | 100 | 13.32 | 26.0 | 700 | 690 | 1.561 | 0.158 |
| 3.2.2.6 inventive | 1.41 | 900 | 300 | 200 | 16.33 | 25.0 | 700 | 690 | 1.561 | 0.127 |
| 3.2.2.7 inventive | 1.69 | 700 | 300 | 100 | 13.32 | 26.0 | 800 | 780 | 1.830 | 0.186 |
| 3.2.2.8 inventive | 1.69 | 700 | 300 | 100 | 13.32 | 26.0 | 700 | 690 | 1.561 | 0.158 |
| 3.2.2.9 inventive | 1.69 | 700 | 300 | 100 | 13.32 | 26.0 | 900 | 870 | 2.099 | 0.213 |
| 3.2.2.10 comparative | 1.69 | 700 | 300 | 100 | 13.32 | 26.0 | 700 | 870 | 0.595 | 0.060 |
| 3.2.2.11 comparative | 1.42 | 2300 | 400 | 400 | 55.46 | 26.0 | 600 | 590 | 1.346 | 0.033 |
| 3.2.2.12 comparative | 1.42 | 2300 | 400 | 400 | 55.46 | 26.0 | 700 | 690 | 1.561 | 0.038 |
| 3.2.2.13 comparative | 1.42 | 2300 | 400 | 400 | 55.46 | 26.0 | 500 | 690 | 0.056 | 0.001 |
| 3.2.2.14 inventive | 1.42 | 2300 | 400 | 400 | 55.46 | 26.0 | 700 | 490 | 2.635 | 0.064 |
| 3.2.2.15 comparative | 1.42 | 2300 | 400 | 400 | 55.46 | 26.0 | 600 | 590 | 1.346 | 0.033 |
| 3.2.2.16 inventive | 1.42 | 2300 | 400 | 400 | 55.46 | 26.0 | 700 | 490 | 2.635 | 0.064 |
| 3.2.2.17 comparative | 1.84 | 2400 | 400 | 500 | 54.90 | 26.0 | 700 | 690 | 1.561 | 0.038 |

TABLE 5-continued

Key catalyst properties with respect to claims

| Example | Carrier BET surface area [m²/g] | Carrier $C_{Si}$ [ppm] | Carrier $C_{Ca}$ [ppm] | Carrier $C_{Mg}$ [ppm] | Carrier R1 [mmol/kg] | Catalyst Ag-content [wt %] | Catalyst Cs-content [ppm] | Catalyst Re-content [ppm] | Catalyst R2 [mmol/kg] | Catalyst R3 |
|---|---|---|---|---|---|---|---|---|---|---|
| 3.2.2.18 inventive | 1.84 | 2400 | 400 | 500 | 54.90 | 26.0 | 1000 | 690 | 3.818 | 0.094 |
| 3.2.2.19 comparative | 1.84 | 2400 | 400 | 500 | 54.90 | 26.0 | 1300 | 690 | 6.076 | 0.150 |
| 3.2.2.20 comparative | 1.84 | 2400 | 400 | 500 | 54.90 | 26.0 | 800 | 780 | 1.830 | 0.045 |
| 3.2.2.21 inventive | 1.84 | 2400 | 400 | 500 | 54.90 | 26.0 | 1130 | 780 | 4.313 | 0.106 |
| 3.2.2.22 comparative | 1.84 | 2400 | 400 | 500 | 54.90 | 26.0 | 1470 | 780 | 6.871 | 0.169 |

3.3. Preparation of Ag Containing Catalysts with an Ag Content of <20 wt.-% (Single Impregnation)

An amount of carrier J listed in Table 6 was placed into a 2 L glass flask. The flask was attached to a rotary evaporator which was set under vacuum pressure of 30 mbar. The rotary evaporator system was set in rotation of 30 rpm. An amount of the silver complex solution listed in Table 6 prepared according to step 3.1 was mixed with an amount of promoter solution I listed in Table 6, an amount of promoter solution II listed in Table 6, an amount of promoter solution III listed in Table 6. Promoter solution I was made from dissolving lithium nitrate (FMC, 99.3%) and ammonium sulfate (Merck, 99.4%) in DI water to achieve target Li and S contents listed in Table 6. Promoter solution II was made from dissolving tungstic acid (HC Starck, 99.99%) in DI water and cesium hydroxide in water (HC Starck, 50.42%) to achieve target Cs and W contents listed in Table 6. Promoter solution III was made from dissolving ammonium perrhenate (Engelhard, 99.4%) in DI water to achieve target Re content listed in Table 6. The combined solution containing silver complex solution, promoter solutions I, II, and III was stirred for 5 minutes. The combined solution was added onto the carrier J over 15 minutes under vacuum of 30 mbar. After addition of the combined solution, the rotary evaporator system was continued to rotate under vacuum for another 15 minutes. The impregnated carrier was then left in the apparatus at room temperature and atmospheric pressure for 1 hour and mixed gently every 15 minutes.

TABLE 6

Catalyst name and amounts of ingredients used for preparation of catalysts 3.3.1 and 3.3.2.

| | Catalyst 3.3.1 (comparative) | Catalyst 3.3.2 (inventive) |
|---|---|---|
| Carrier name | Carrier J | Carrier J |
| Amount of carrier [g] | 174.2 | 174.1 |
| Amount of Ag-complex solution [g] | 109.6222 | 109.5749 |
| Ag-content in Ag-complex solution [wt %] | 29.2 | 29.2 |
| Amount of promoter solution I [g] | 1.3768 | 1.3762 |
| Li-/S-content in promoter solution I [wt %] | 2.85/0.21 | 2.85/0.21 |
| Amount of promoter solution II [g] | 2.0651 | 2.0642 |
| Cs-/W-content in promoter solution II [wt %] | 4.8/2.0 | 6.0/2.0 |
| Amount of promoter solution III [g] | 3.2931 | 2.9705 |
| Re-content in promoter solution III [wt %] | 3.7 | 4.1 |

Catalyst compositions are listed in Table 7.

TABLE 7

Catalyst compositions (Ag-contents are reported in percent by weight of total catalyst, dopant values are reported in parts per million by weight of total catalyst)

| Example | Carrier | Ag [wt-%] | Li [ppm] | S [ppm] | W [ppm] | Cs [ppm] | Re [ppm] |
|---|---|---|---|---|---|---|---|
| 3.3.1 (comparative) | J | 15.5 | 190 | 14 | 200 | 480 | 590 |
| 3.3.2 (inventive) | J | 15.5 | 190 | 14 | 200 | 600 | 590 |

TABLE 8

Key catalyst properties with respect to claims

| Example | Carrier BET surface area [m²/g] | Carrier $C_{Si}$ [ppm] | Carrier $C_{Ca}$ [ppm] | Carrier $C_{Mg}$ [ppm] | Carrier R1 [mmol/kg] | Catalyst Cs-content [ppm] | Catalyst Re-content [ppm] | Catalyst R2 [mmol/kg] | Catalyst R3 |
|---|---|---|---|---|---|---|---|---|---|
| 3.3.1 (comparative) | 1.06 | 700 | 300 | 100 | 13.32 | 480 | 590 | 0.443 | 0.039 |
| 3.3.2 (inventive) | 1.06 | 700 | 300 | 100 | 13.32 | 600 | 590 | 1.346 | 0.120 |

4. Catalyst Testing I

The epoxidation reaction was conducted in a vertically-placed test reactor constructed from stainless steel with an inner-diameter of 6 mm and a length of 2.2 m. The reactor was heated using hot oil contained in a heating mantel at a specified temperature. All temperatures below refer to the temperature of the hot oil. The reactor was filled to a height of 212 mm with inert steatite balls (1.0-1.6 mm), then packed to a height of 1100 mm with split catalyst (particle size 0.5-0.9 mm) and then again packed with an additional 707 mm inert steatite balls (1.0-1.6 mm). The inlet gas was introduced to the top of the reactor in a "once-through" operation mode.

The inlet gas consisted of about 35 vol % ethylene, 7 vol % oxygen, 1 vol % $CO_2$, and ethylene chloride (EC) moderation in the range from 1.5 to 3.5 parts per million by volume (ppmv), with methane used as a balance. The reactions were conducted at a pressure of about 15 bar and a GHSV of about 4800 $h^{-1}$. For catalysts with an Ag content of >20 wt.-% (catalysts 3.2.2.1 to 3.2.2.22), the temperature and ethylene chloride (EC) moderation were adjusted such that a work rate of 280 kg(EO)/($m^3$(catalyst)×h) was obtained at the highest EO selectivity. For catalysts with an Ag content of <20 wt.-% (catalysts 3.3.1 and 3.3.2), the temperature and ethylene chloride (EC) moderation were adjusted such that a work rate of 250 kg(EO)/($m^3$(catalyst)×h) was obtained at the highest EO selectivity.

Results of the catalyst tests with catalysts containing >20 wt.-% of Ag are shown in Table 9. The results show that the catalysts of the inventive Examples 3.2.2.3, 3.2.2.4, 3.2.2.5 and 3.2.2.6 have a significantly improved activity (measured as temperature to maintain the work rate) over the catalysts of the comparative Examples 3.2.2.2 and 3.2.2.15.

TABLE 9

Test reaction results

| Catalyst | Carrier | EO-Selectivity [%] | Temperature [° C.] | Time on stream [d] |
|---|---|---|---|---|
| 3.2.2.2 comparative | B | 88.3 | 230.6 | 14 |
| 3.2.2.2 comparative | B | 89.3 | 233.5 | 21 |
| 3.2.2.2 comparative | B | 89.4 | 238.3 | 30 |
| 3.2.2.3 inventive | C | 89.6 | 228.1 | 21 |
| 3.2.2.3 inventive | C | 90.1 | 230.0 | 30 |
| 3.2.2.4 inventive | D | 89.7 | 229.7 | 14 |
| 3.2.2.5 inventive | E | 89.5 | 232.8 | 21 |
| 3.2.2.5 inventive | E | 89.5 | 231.4 | 30 |
| 3.2.2.6 inventive | F | 89.8 | 232.0 | 14 |
| 3.2.2.15 comparative | H | 88.5 | 232.9 | 14 |
| 3.2.2.16 inventive | H | 88.5 | 228.9 | 14 |

Results of the catalyst tests with catalysts containing <20 wt.-% of Ag are shown in Table 10. The results show that the catalyst of the inventive Example 3.3.2 has a significantly improved activity (measured as temperature to maintain the work rate) over the catalysts of the comparative Examples 3.3.1.

TABLE 10

Test reaction results for catalysts with Ag contents of <20 wt.-%.

| Catalyst | Carrier | EO-Selectivity [%] | Temperature [° C.] | Time on stream [d] |
|---|---|---|---|---|
| 3.3.1 comparative | J | 88.2 | 247.5 | 8 |
| 3.3.1 comparative | J | 89.4 | 246.5 | 16 |
| 3.3.2 inventive | J | 90.7 | 237.1 | 8 |
| 3.3.2 inventive | J | 90.9 | 237.9 | 16 |

5. Catalyst Testing II

The catalyst screening was performed in a 16-fold parallel reactor system. Every reactor was simultaneously supported with the same inlet gas, temperature and pressure.

The used reactor tubes were composed of stainless steel (1.4841) and had a length of 290 mm with an outer diameter of 10 mm and an inner diameter of 4.5 mm. The isothermal zone of the reactor has a length of 70 mm and this was heated using an indirect electrical heating. 1 mL catalyst with a particle size of 250 μm to 300 μm was placed in the isothermal zone of the reactor tube.

The filling concept of the reactor tube is described in table 11. The filling concept is a stacked bed with five individual zones. From reactor top to bottom the reactor filling consist of two inert stacks from steatite beads and silica particles, followed by the catalyst located in the isothermal zone in the center of the reactor tube, followed by another two inert stacks, consisting of silica particles and steatite beads. Zone 5 represents the top of the reactor tube, where the inlet gas was introduced into the reactor tube and conducted in once-through operation mode.

TABLE 11

Reactor tube filling

| Zone | Height [mm] | Material | Particle size [μm] |
|---|---|---|---|
| 1 | 0-70 | steatite beads | 315-500 |
| 2 | 70-60 | silica particles | 200-300 |
| 3 | 90-153 | catalyst | 250-300 |
| 4 | 153-173 | silica particles | 200-300 |
| 5 | 173-290 | steatite beads | 315-500 |

The experiments were carried out at a GHSV of 4850 $h^{-1}$, a reactor pressure of 15 barg and a reactor temperature of 230° C. The inlet gas consists of 35 vol. % ethylene, 7 vol. % oxygen, 5 vol. % argon and ethyl chloride (EC), which was dosed over a range of 1.25 to 2.5 ppmv. Nitrogen was used as carrier gas and argon as internal standard gas.

The reactor outlet gas was quenched with nitrogen at a ratio of 2:1 to 4:1 and was analyzed via online gas chromatography (GC).

Tests were carried out at reactor temperatures of 230° C. and ethylene chloride concentrations of 1.25 ppmv and 2.5 ppmv. The results of the catalyst screening are shown in Table 12.

TABLE 12

Test reaction results.

| Catalyst | Carrier | Temperature [° C.] | EC [ppm] | EO yield [%] |
|---|---|---|---|---|
| 3.2.2.1 (comparative) | A | 230 | 2.5 | 6.23 |
| 3.2.2.7 (inventive) | G | 230 | 2.5 | 10.21 |
| 3.2.2.8 (inventive) | G | 230 | 2.5 | 9.82 |
| 3.2.2.9 (inventive) | G | 230 | 2.5 | 10.22 |
| 3.2.2.10 (comparative) | G | 230 | 2.5 | 7.58 |
| 3.2.2.11 (comparative) | H | 230 | 2.5 | 7.26 |
| 3.2.2.12 (comparative) | H | 230 | 2.5 | 6.83 |
| 3.2.2.13 (comparative) | H | 230 | 2.5 | 6.95 |
| 3.2.2.14 (inventive) | H | 230 | 2.5 | 9.16 |
| 3.2.2.17 (comparative) | I | 230 | 2.5 | 7.93 |
| 3.2.2.18 (inventive) | I | 230 | 2.5 | 9.92 |
| 3.2.2.19 (comparative) | I | 230 | 2.5 | 6.91 |
| 3.2.2.20 (comparative) | I | 230 | 2.5 | 7.36 |
| 3.2.2.21 (inventive) | I | 230 | 2.5 | 9.30 |
| 3.2.2.22 (comparative) | I | 230 | 2.5 | 6.13 |
| 3.2.2.1 (comparative) | A | 230 | 1.25 | 6.25 |
| 3.2.2.7 (inventive) | G | 230 | 1.25 | 10.74 |
| 3.2.2.8 inventive) | G | 230 | 1.25 | 10.48 |
| 3.2.2.9 (inventive) | G | 230 | 1.25 | 10.69 |
| 3.2.2.10 (comparative) | G | 230 | 1.25 | 7.38 |
| 3.2.2.11 (comparative) | H | 230 | 1.25 | 6.80 |
| 3.2.2.12 (comparative) | H | 230 | 1.25 | 6.00 |
| 3.2.2.13 (comparative) | H | 230 | 1.25 | 5.51 |
| 3.2.2.14 (inventive) | H | 230 | 1.25 | 9.71 |
| 3.2.2.17 (comparative) | I | 230 | 1.25 | 6.61 |
| 3.2.2.18 (inventive) | I | 230 | 1.25 | 9.38 |
| 3.2.2.19 (comparative) | I | 230 | 1.25 | 7.56 |
| 3.2.2.20 (comparative) | I | 230 | 1.25 | 5.14 |
| 3.2.2.21 (inventive) | I | 230 | 1.25 | 9.04 |
| 3.2.2.22 (comparative) | I | 230 | 1.25 | 6.67 |

The invention claimed is:

1. A shaped catalyst body for preparing ethylene oxide, which comprises silver, cesium and rhenium applied to an alumina support, wherein the alumina support comprises Si with the Si content in the carrier being defined as $C_{Si}$ and measured in ppm per total support weight, Ca with the Ca content in the carrier being defined as $C_{Ca}$, and measured in ppm per total support weight, and Mg with the Mg content in the carrier being defined as $C_{Mg}$ and measured in ppm per total support weight, wherein the value of the expression $R1=C_{Si}/AW_{Si}-C_{Ca}/AW_{Ca}-C_{Mg}/AW_{Mg}$ is in the range of 1 to 100 mmol/kg per weight of the carrier, and $AW_{Si}$, $AW_{Ca}$, and $AW_{Mg}$ relate to atomic weight of Si, Ca and Mg in g/mol, respectively, and wherein the catalyst comprises Ag with the Ag content in the catalyst being defined as $C_{Ag}$ and measured in weight percent per total catalyst weight, Cs with the Cs content in the catalyst being defined as $C_{Cs}$ and measured in ppm per total catalyst weight, Re with the Re content in the catalyst being defined as $C_{Re}$ and measured in ppm per total catalyst weight, wherein the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$, relate to atomic weight of Cs and Re in g/mol, respectively and the value of the expression $R3=R2/[R1\times(100-C_{Ag})/100]$ is in the range of 0.05 to 1, and further comprising rhenium, and cesium, in amounts such that the rhenium content $C_{Re}$ exceeds 450 ppm per weight of the total catalyst, and the cesium content $C_{Cs}$ exceeds 450 ppm per weight of the total catalyst.

2. The shaped catalyst body according to claim 1, wherein the Si content in the carrier $C_{Si}$ is in the range from 200 to 4000 ppm based on the total weight of the support and calculated as element.

3. The shaped catalyst body according to claim 1, wherein the Ca content in the carrier $C_{Ca}$ is in the range from 100 to 1000 ppm based on the total weight of the support and calculated as element.

4. The shaped catalyst body according to claim 1, wherein the alumina support comprises up to 1000 ppm of magnesium, based on the total weight of the support and calculated as element.

5. The shaped catalyst body according to any of claim 1, wherein the alumina support has a BET surface area in the range from 0.95 to 3.0 m$^2$/g.

6. The shaped catalyst body according to claim 1, wherein the alumina support has at least two pore size distributions wherein at least one of the pore size distributions is within a pore size range of about 0.1 to 5 μm.

7. The shaped catalyst body according to claim 1, wherein the shaped catalyst body comprises silver in an amount of from 5 to 40% by weight, based on the total weight of the shaped catalyst body and calculated as element.

8. The shaped catalyst body according to claim 1, wherein the catalyst comprises at least one promoter selected from the group consisting of elements of groups IA, VIB, VIIB and VIA.

9. The shaped catalyst body according to claim 1, wherein the value of the expression R1 is in the range of 5 to 75 mmol/kg per weight of the carrier.

10. The shaped catalyst body according to claim 1, wherein the value of the expression R1 is in the range of 10 to 60 mmol/kg per weight of the carrier.

11. The shaped catalyst body according to claim 1, wherein the catalyst comprises at least one promoter selected from the group consisting of tungsten, lithium and sulfur.

12. The shaped catalyst body according to claim 1, wherein the value of the expression R2 is in the range of 1.346 to 5.0 mmol/kg per weight of total catalyst.

13. A process for preparing ethylene oxide by gas-phase oxidation of ethylene by means of oxygen in the presence of a shaped catalyst body according to claim 1.

14. A process for producing a shaped catalyst body comprising silver and rhenium applied to an alumina support, which comprises (a) providing an alumina support;
(b) applying silver, cesium and rhenium to the alumina support, wherein for the alumina support, the value of the expression $R1=C_{Si}/AW_{Si}-C_{Ca}/AW_{Ca}-C_{Mg}/AW_{Mg}$ is in the range of 1 to 100 mmol/kg per weight of the carrier, and $AW_{Si}$, $AW_{Ca}$, and $AW_{Mg}$ relate to atomic weight of Si, Ca and Mg in g/mol, respectively, and and rhenium and cesium are applied in amounts such that the value of the expression $R2=C_{Cs}/AW_{Cs}-C_{Re}/AW_{Re}$ is in the range of 1.0 to 5.0 mmol/kg per weight of total catalyst, and $AW_{Cs}$, and $AW_{Re}$ relate to atomic weight of Cs and Re in g/mol, respectively and the value of the expression $R3=R2/[R1\times(100-CAg)/100]$ is in the range of 0.05 to 1, and further comprising rhenium, and cesium, in amounts such that the rhenium content $C_{Re}$ exceeds 450 ppm per weight of the total catalyst, and the cesium content $C_{Cs}$ exceeds 450 ppm per weight of the total catalyst.

15. The process according to claim 14, wherein the process further comprises (c) calcining the alumina support obtained according to (b).

16. The process according to claim 14, wherein silver is applied in an amount of from 5 to 35% by weight, based on the total weight of the shaped catalyst body and calculated as element, in (b).

17. The process according to claim 14, wherein for the alumina support, the value of the expression R1 is in the range of 5 to 75 mmol/kg per weight of the carrier.

18. The process according to claim 14, wherein for the alumina support, the value of the expression R1 is in the range of 10 to 60 mmol/kg per weight of the carrier.

19. A shaped catalyst body obtained by the process according to claim 14.

* * * * *